(12) United States Patent
Yaginuma et al.

(10) Patent No.: US 9,095,512 B2
(45) Date of Patent: Aug. 4, 2015

(54) METHOD FOR PRODUCING SPHERICAL BASE GRANULES COMPRISING HARDLY WATER-SOLUBLE DRUG

(75) Inventors: Yoshihito Yaginuma, Tokyo (JP); Rika Matsumoto, Tokyo (JP)

(73) Assignee: ASAHI KASEI CHEMICALS CORPORATION, Tokyo (JP)

( * ) Notice: Subject to any disclaimer, the term of this patent is extended or adjusted under 35 U.S.C. 154(b) by 1039 days.

(21) Appl. No.: 12/310,067

(22) PCT Filed: Aug. 9, 2007

(86) PCT No.: PCT/JP2007/065654
§ 371 (c)(1),
(2), (4) Date: Feb. 10, 2009

(87) PCT Pub. No.: WO2008/018561
PCT Pub. Date: Feb. 14, 2008

(65) Prior Publication Data
US 2009/0324802 A1 Dec. 31, 2009

(30) Foreign Application Priority Data
Aug. 11, 2006 (JP) .................................. 2006-220247

(51) Int. Cl.
*A61K 9/28* (2006.01)
*A61K 9/16* (2006.01)
(Continued)

(52) U.S. Cl.
CPC .............. *A61K 9/1676* (2013.01); *A61K 9/1694* (2013.01); *A61K 31/166* (2013.01); *A01N 43/56* (2013.01); *A61K 9/14* (2013.01)

(58) Field of Classification Search
CPC .......... A61K 31/655; A61K 9/14; A61K 9/48; A61K 9/16; A61K 9/24; A61K 9/32; A61K 31/445; A01N 59/14; A01N 43/56; A01N 43/40; C08B 3/32
USPC .......... 514/404, 912, 150, 277, 336, 337, 338, 514/330; 424/489, 451, 452, 490, 493, 494, 424/659, 472; 536/57, 60, 61
See application file for complete search history.

(56) References Cited

U.S. PATENT DOCUMENTS 4,902,792 A * 2/1990 Okuma et al. ................. 536/57
5,026,560 A 6/1991 Makino et al.
(Continued)

FOREIGN PATENT DOCUMENTS

JP 63-301816 12/1988
JP 9-67247 3/1997
(Continued)

OTHER PUBLICATIONS

Erikkson, Voltammetric Properties of Olsalzaine Sodium and some Related Compounds, 2001, ACTA Universitatis Upsaliensis Uppsala, vol. 638, pp. 1-38.*

(Continued)

*Primary Examiner* — Dah-Wei D Yuan
*Assistant Examiner* — Andrew Bowman
(74) *Attorney, Agent, or Firm* — Staas & Halsey LLP

(57) ABSTRACT

Spherical base granules comprising a hardly water-soluble drug and suited for film coating thereon are produced by layering spherical core particles with a drug-containing layering liquid comprising both micronized microcrystalline cellulose and an emulsifier therein and therefore having improved suspension stability.

14 Claims, 3 Drawing Sheets

(51) Int. Cl.
*A61K 31/166* (2006.01)
*A01N 43/56* (2006.01)
*A61K 9/14* (2006.01)

(56) References Cited

U.S. PATENT DOCUMENTS

| | | | |
|---|---|---|---|
| 5,516,531 | A | 5/1996 | Makino et al. |
| 5,837,723 | A * | 11/1998 | Watanabe ................ 514/404 |
| 5,855,914 | A | 1/1999 | Koyama et al. |
| 6,156,771 | A * | 12/2000 | Rubin et al. ................ 514/330 |
| 6,228,400 | B1 * | 5/2001 | Lee et al. ................ 424/489 |
| 2001/0003003 | A1 * | 6/2001 | Yamaguchi et al. .......... 424/659 |
| 2002/0098235 | A1 * | 7/2002 | Dittmar et al. ............. 424/472 |
| 2005/0090473 | A1 * | 4/2005 | Devane et al. ............. 514/150 |
| 2005/0129760 | A1 | 6/2005 | Muskulus et al. |

FOREIGN PATENT DOCUMENTS

| | | |
|---|---|---|
| JP | 9-165329 | 6/1997 |
| JP | 2005-536527 | 12/2005 |
| WO | 2005/044240 A2 | 5/2005 |

OTHER PUBLICATIONS

Li et al., Preparation of a Controlled Release Drug Delivery System of Indomethacin: Effect of Process Equipment, Particle Size of Indomethacin, and Size of NonPareil Seeds, 1989, Drug Development and Industrial Pharmacy, 15 (8), pp. 1137-1159.*

Unknown, Products—Nonpareil Seeds and Sugar Spheres, 2014, Mayon's Pharmaceutical Pvt. Ltd., http://www.mayons.com/nonpareil_seeds.html.*

European Search Report for related European Patent Application No. 07 79 2304, mailed Aug. 9, 2011.

Hsiu-O Ho et al., "Influence of pluronic F-68 on dissolution and bioavailability characteristics of multiple-layer pellets of nifedipine for controlled release delivery", Journal of Controlled Release, No. 68, Elsevier, May 20, 2000, pp. 433-440.

International Search Report (International Application No. PCT/JP2007/065654; International Search Report mailing date: Nov. 20, 2007).

English Translation of the International Preliminary Report on Patentability issued on Feb. 26, 2009 in corresponding International Patent Application PCT/JP2007/065654.

European Office Action for corresponding European Patent Application No. 07792304.3, issued Sep. 18, 2013, 9 pages.

Daniel Limmer, Editor, "Remington: The Science and Practice of Pharmcay, 20$^{th}$ Edition," Lippincott Williams & Wilkins, 2000, 5 pages. (Title Page, Copyright Page, pp. 1030-1032).

Michael Levin, Editor, "Pharmaceutical Process Scale-Up," Marcel Dekker, inc., 2002, 3 pages (Title Page, Copyright Page, p. 147).

Raymond C. Rowe et al., Editors, "Handbook or Pharmaceutical Excipients, Fifth Edition," Pharmaceutical Press, 2005, 3 pages (Title Page, Information page from Amazon.com, page from reference).

* cited by examiner

METHOD FOR PRODUCING SPHERICAL BASE GRANULES COMPRISING HARDLY WATER-SOLUBLE DRUG

CROSS REFERENCE TO RELATED APPLICATIONS

This application claims the benefit under 35 U.S.C. Section 371, of PCT International Application No. PCT/JP2007/065654, filed Aug. 9, 2007, which claimed priority to Japanese Application No. 2006-220247, filed Aug. 11, 2006, in the Japanese Patent Office, the disclosures of all of which are incorporated herein by reference.

TECHNICAL FIELD

The present invention relates to a production method of spherical base granules comprising a hardly water-soluble drug.

BACKGROUND ART

Pharmaceutical solid preparations sometimes have sustained release, enteric, or bitterness-masking film coating with a view to reducing side effects of a drug comprising in them, reducing the administration frequency, improving the effect of the drug, suppressing a bitter taste, stabilizing the drug, or the like. Drug-containing spherical granules having a dosage form suited for film coating thereon are called spherical base granules.

As a production method of spherical base granules, a method of carrying out extrusion granulation using a drug and an excipient as raw materials and then spheronizing the resulting granule product (extrusion-spheronization method), a method of coating the surface of spherical core particles with a drug (layering method) (refer to, for example, Patent Document 1), and the like are known.

In the layering method, granules are produced by spraying a layering liquid comprising a drug, a binder, and the like to spherical core particles to coat them with a coating layer. Specific examples of it include a method of simultaneously supplying drug powders and an aqueous solution of a binder and coating spherical core particles with them; a method of supplying a suspension of drug particles and coating the spherical core particles therewith; and a method of supplying an aqueous solution of a drug and coating the spherical core particles therewith.

The layering method is suited as a method for producing spherical base granules to be film-coated, because spherical base granules having a high sphericity and a narrow particle size distribution can be obtained using spherical core particles having a high sphericity and a narrow particle size distribution.

However, when a drug that is contained in the layering liquid has low water solubility (hardly water-soluble drug), dispersion in an apparatus having a high shear force is necessary to obtain a uniform suspension. Therefore, when such a layering liquid is prepared, vigorous foaming occurs, and foam breaking is sometimes necessary. In addition, in a layering liquid having a practical drug concentration, the drug particles precipitate with the passage of time. The layering liquid therefore must be stirred/mixed constantly to keep the suspension uniform. Even if the layering liquid is stirred/mixed constantly, there is a risk of a tube or spray nozzle being clogged with precipitated/agglomerated particles during a transfer of the layering liquid from a tank to the spray nozzle. When the drug has a large particle size, the above risk increases further, which leads to deterioration in adhesion to spherical core particles, a reduction in a recovery ratio, and an increase in agglomeration ratio due to inhibition of smooth tumbling. A reduction in the size of the drug particles improves suspension stability of the layering liquid and a recovery ratio, but it needs an extra pulverization (or grinding) treatment step of the drug particles.

It is known to add various additives to the layering liquid for the purpose of preventing detachment of the coated drug, controlling a dissolution rate of the drug, or stabilizing the layering liquid (refer to, for example, Patent Documents 2, 3, and 4). These prior arts however fail to improve the suspensibility of a hardly water-soluble drug. Patent Documents 2 to 4 include no description on the use of both micronized microcrystalline cellulose and an emulsifier in combination Patent Document 5 discloses a technology of coating spherical core particles with a hardly water-soluble drug, an emulsifier, and the like in accordance with the layering method, but the technology specifically disclosed herein is a layering method in which drug powders and an aqueous solution of a binder are supplied simultaneously to coat therewith the particles. Patent Document 5 includes no description on the improvement of suspensibility during addition of a hardly water-soluble drug to a layering liquid.

Patent Document 1: Japanese Patent Application Laid-Open No. 63-301816
Patent Document 2: Japanese Patent Application Laid-Open No. 9-165329
Patent Document 3: Japanese Patent Application Laid-Open No. 9-67247
Patent Document 4: Published Japanese translation of PCT international publication No. 2005-536527
Patent Document 5: International Publication No. 2005/044240

DISCLOSURE OF THE INVENTION

Problems to be Solved by the Invention

An object of the present invention is to provide a method of producing, with an improved production efficiency, spherical base granules comprising a hardly water-soluble drug by using a layering liquid comprising the hardly water-soluble drug, having good suspension stability, and controlled to minimize foaming.

Means for Solving the Problem

The present inventors have carried out an extensive investigation with a view to overcoming the above-described problem. As a result, it has been found that by adding micronized microcrystalline cellulose and an emulsifier in a layering liquid, suspension stability of the layering liquid is improved and foaming is suppressed without extra pulverization treatment of a drug, leading to the completion of the present invention. The following is the details of the present invention.

A production method of spherical base granules comprising a hardly water-soluble drug, which comprises spraying a layering liquid to pharmaceutically inert spherical core particles and coating the particles with a drug-containing layer, wherein the layering liquid comprises:

(1) from 0.01 to 50% by mass of hardly water-soluble drug particles having a maximum long diameter and a maximum short diameter of not greater than 30% and not greater than 12% of an average short diameter of the spherical core particles, respectively;

(2) from 0.1 to 2% by mass of micronized microcrystalline cellulose; and (3) from 0.01 to 1% by mass of an emulsifier.

Advantage of the Invention

The method according to the present invention enables stable production of spherical base granules comprising a hardly water-soluble drug with high productivity.

BEST MODE FOR CARRYING OUT THE INVENTION

The present invention will hereinafter be described specifically.

The spherical core particles to be used in the present invention are pharmaceutically inert. This means that the core particles do not comprise a drug.

The term "drug" as used herein means what is used for treatment, prevention, or diagnosis of human or animal diseases but what is not an instrument/machine.

The spherical core particles may contain one or more pharmaceutical additive. Examples of such a pharmaceutical additive include excipients such as lactose, sucrose, D-mannitol, corn starch, powder cellulose, calcium hydrogen phosphate, and calcium carbonate; disintegrants such as low-substituted hydroxypropyl cellulose, carmellose calcium, pregelatinized starch, croscarmellose sodium, crospovidone, and carboxymethyl starch; binders such as hydroxypropyl cellulose, povidone (polyvinylpyrrolidone), and xanthan gum; coating agents such as hypromelose (hydroxypropylmethyl cellulose), methacrylic acid copolymer LD, and ethylcellulose aqueous dispersion; emulsifiers such as sucrose fatty acid ester, glycerin fatty acid ester, sodium lauryl sulfate, and polysorbate 60; and other additives such as talc, magnesium stearate, magnesium aluminometasilicate, titanium oxide, light silicic anhydride, microcrystalline cellulose-carmellose sodium.

Preferred examples of a formulation include spherical core particles composed only of sucrose, those composed of 70% by mass of sucrose and 30% by mass of corn starch, those composed of 30% by mass or more of microcrystalline cellulose and another pharmaceutical additive, those composed only of microcrystalline cellulose, and those composed only of mannitol. Spherical core particles comprising 30% by mass or more of microcrystalline cellulose are preferred because of having high strength and high water absorption capacity. Those comprising 70% by mass or more of microcrystalline cellulose are more preferred, with spherical core particles composed only of crystalline cellulose being still more preferred. Spherical core particles composed only of microcrystalline cellulose are most preferred.

The term "spherical" of spherical core particles means that the particles have a sphericity or (short diameter/long diameter (minor axis/major axis) ratio of 0.7 or greater. As such, some "elliptical" particles fall within this definition. Particles which are not spherical are not preferred because they deteriorate uniformity of film coating. The spherical core particles having a sphericity of 0.9 or greater are preferred.

As the spherical core particles, those having an average particle size of from about 50 to 1000 μm can be used. The particle size distribution is preferably sharp. The bulk density is preferably from about 0.5 to 2.0 g/cm$^3$. The spherical core particles composed only of microcrystalline cellulose have generally a bulk density of from about 0.5 to 1.0 g/cm$^3$. The mechanical strength is preferably higher.

The layering liquid to be used in the present invention will next be described.

First, hardly water-soluble drug particles to be incorporated in the layering liquid of the present invention will be described.

The term "hardly water-soluble" as used herein means that the particles do not dissolve in water readily and they have solubility, in 1 cm$^3$ of water at 20° C., of 0.001 g or less.

Examples of the hardly water-soluble drug include amcinonide, ibuprofen, indomethacin, ethenzamide, erythromycin, cefotiam hexetil hydrochloride, nicardipine-hydrochloride, omeprazole, prednisolone valerate acetate, diflucortolone valerate, dexamethasone valerate, betamethasone valerate, clarithromycin, griseofulvin, clonazepam, chloramphenicol, synthetic peptide compounds, cortisone acetate, diflorasone diacetate, dexamethasone acetate, triamcinolone acetate, paramethasone acetate, hydrocortisone acetate, fludrocortisone acetate, methylprednisolone acetate, diazepam, digitoxin, digoxin, difluprednate, beclometasone dipropionate, betamethasone dipropionate, sulpiride, sulfathiazole, cefuroxime axetil, dexamethasone, triamcinolone, triamcinolone acetonide, nicardipine, nifedipine, nilvadipine, noscapine, halcinonide, hydrocortisone, flumetasone pivalate, phenacetin, phenitoin, budesonide, prazepam, fluocinonide, fluocinolone acetonide, fluorometholone, fludroxycortide, prednisolone, alclometasone dipropionate, clobetasol propionate, dexamethasone propionate, deprodone propionate, betamethasone, migrenin, methylprednisolone, ubidecarenone, clobetasone butyrate, hydrocortisone butyrate, hydrocortisone butyrate propionate, riboflavin butyrate, lansoprazole, and riboflavin.

The hardly water-soluble drug particles are preferably smaller. The maximum long diameter of them is 30% or less of the average short diameter of the spherical core particles and the maximum short diameter is 12% or less of the average short diameter of the spherical core particles. When each of the diameters exceeds the specified values, respectively, the drug particles are likely to detach from the spherical base granules, and the recovery ratio of the spherical base granules will decrease. In addition, presence of the drug particles detached from the granules inhibits tumbling of the spherical core particles, resulting in an increase in agglomeration of the spherical base granules.

The maximum long diameter of the drug particles is preferably not greater than 20% of the average short diameter of the spherical core particles and the minimum short diameter of the drug particles is preferably not greater than 10%.

The hardly water-soluble particles are added to the layering liquid in an amount of from 0.01 to 50% by mass. When the amount is less than 0.01% by mass, layering need to be performed for long hours to coat the spherical core particles with a necessary amount of the drug. When it exceeds 50% by mass, on the other hand, the viscosity of the layering liquid becomes too high and prevents smooth spraying. It is preferably from 1 to 30% by mass, more preferably from 5 to 20% by mass.

The micronized microcrystalline cellulose to be incorporated in the layering liquid of the present invention will hereinafter be described.

The term "micronized microcrystalline cellulose" to be incorporated in the layering liquid in the present invention means microcrystalline cellulose having an average particle size of 12 μm or less as measured in water. It is more preferably 9 μm or less.

The term "microcrystalline cellulose" as used herein means that conforms to any of the standards "Microcrystalline cellulose" specified in the Japanese Pharmacopoeia, Fifteenth Edition, "Microcrystalline cellulose" specified in Japanese Standards of Food Additives, Seventh Edition, and "Microcrystalline cellulose-carmellose sodium" specified in Japanese Pharmaceutical Excipients 2003.

The micronized microcrystalline cellulose is, for example, that obtained by dry or wet grinding of typical microcrystalline cellulose or that obtained by dispersing microcrystalline cellulose-carmellose sodium in water. Microcrystalline cellulose-carmellose sodium is preferred because a layering liquid comprising it can be prepared easily and at the same time, has high suspension stability, and spherical base granules available using it have high strength.

The micronized microcrystalline cellulose is added to the layering liquid in an amount of from 0.1 to 2% by mass. When the amount is less than 0.1% by mass, a sufficient suspension stabilizing effect is not obtained. When it exceeds 2% by mass, on the other hand, the layering liquid has a too high viscosity and cannot be sprayed smoothly. It is preferably from 0.2 to 1% by mass, more preferably from 0.3 to 0.8% by mass.

Addition of the micronized microcrystalline cellulose to the layering liquid improves suspension stability of the hardly water-soluble drug particles in the layering liquid and solves the problem of clogging a tube and also a spray nozzle therewith. Moreover, it improves the adhesion of the hardly water-soluble drug particles to the spherical core particles so that it is also effective for raising a recovery ratio and reducing an agglomeration ratio.

An emulsifier that can be comprised in the layering liquid of the present invention will next be described.

In the present invention, the term "emulsifier" that may be comprised in the layering liquid means a substance having an emulsifying function to be used for the preparation of pharmaceutical formulations.

Examples of the emulsifier include sucrose fatty acid esters, glycerin fatty acid esters, sodium lauryl sulfate, polysorbates, polyoxyethylene hydrogenated castor oils, carmellose sodium, and xanthan gum. The emulsifier is adequately selected, depending on the physical properties of the drug particles. Of these, polyoxyethylene hydrogenated castor oils are preferred from the viewpoint of their high foaming suppressing effect, with polyoxyethylene hydrogenated castor oil 60 being more preferred. The polyoxyethylene hydrogenated castor oil 60 is a nonionic surfactant obtained by addition polymerization of a hydrogenated castor oil with ethylene oxides and having an average molar number of added ethylene oxide of about 60. It has a CAS No. of 61788-85-0. The average molar number of ethylene oxide added to polyoxyethylene hydrogenated castor oil 60 is preferably from 52 to 68, more preferably from 55 to 65.

The emulsifier is added to the layering liquid in an amount of from 0.01 to 1% by mass. Amounts less than 0.01% by mass do not sufficiently improve the affinity of the drug particles with water. Although there is no upper limit for the additive amount of emulsifier, the effect is not enhanced as much as expected when the additive amount exceeds 1% by mass or greater. The amount is more preferably from 0.05 to 0.8% by mass.

Addition of the emulsifier to the layering liquid raises affinity of the drug particles with water, thereby suppressing foaming. Due to a synergetic effect of the emulsifier and micronized microcrystalline cellulose, the layering liquid becomes a stable suspension. Only slight stirring or, in some cases, no stirring is therefore necessary for maintaining the suspension state of the layering liquid.

To a suspension such as a suspension syrup or dry syrup comprising sucrose at a concentration of 20% by mass or a concentration as high as about 5% by mass or greater, microcrystalline cellulose-carmellose sodium and an emulsifier such as polysorbate have been sometimes added in combination in order to improve suspension stability. However, a problem of foaming does not originally happen in such a suspension, as it contains sucrose at a high concentration. Therefore, for those skilled in the art, it is unexpected that combination use of an emulsifier and micronized microcrystalline cellulose in the layering liquid that does not comprise sucrose at high concentration produces not only a suspension stabilization effect but also an excellent foaming suppressing effect.

Another pharmaceutical additive may be added to the layering liquid as needed. In particular, addition of a binder is especially preferred because it improves the strength of the drug-containing layer. Examples of the binder include hydroxypropyl cellulose, povidone, and hypromelose (hydroxypropylmethyl cellulose).

A process of coating the spherical core particles with a layer comprising the hardly water-soluble drug by layering will next be described.

Fluidized-bed coating apparatuses can be used for coating the spherical core particles with the layer comprising a hardly water-soluble drug. Examples of the fluidized-bed coating apparatus include, in addition to an ordinary fluidized bed type, a spouted fluidized-bed type having, inside thereof, a guide tube (Wurster column) and a tumbling fluidized-bed type equipped, on the bottom thereof, a rotation mechanism.

Specific examples of such apparatuses include "Flow Coater" and "Spiral Flow", products of Freund Corporation, "WST/WSG Series" and "GPCG Series", products of Glatt GmbH, "New Marumerizer", product of Fuji Paudal Co., Ltd., and "Multiplex", product of Powrex Corporation.

The layering liquid can be supplied by a method suited for each of apparatuses such as top spray, bottom spray, side spray, and tangential spray. It may be sprayed to the spherical core particles continuously or intermittently. After completion of spraying, the spherical base granules are dried. Drying of the spherical base granules may be performed as are or after controlling an air flow rate or temperature as needed, while not taking out the granules from the apparatus.

The coating amount of the drug-containing layer can be determined based on the formulation design such as single dosage or size of the preparation. For example, it is generally from about 0.5 to 200% by mass relative to the spherical core particles.

Next, one example of a production method of the spherical base granules will be described.

(a) Preparation of micronized microcrystalline cellulose: First, microcrystalline cellulose is dispersed in water and the resulting aqueous dispersion is micronized in a Manton-Gaulin Homogenizer. Micronization=treatment is performed for necessary times at high pressure, for example, at 50 MPa and five passes. When micronized microcrystalline cellulose (for example, "CEOLUS Cream" FP-03, product of Asahi Kasei Chemicals Corporation, solid content: 10% by mass, average particle size: about 4 µm) or microcrystalline cellulose-carmellose sodium (for example, "CEOLUS" RC-A591 NF, product of Asahi Kasei Chemicals Corporation) is used, the micronization step is not necessary.

(b) Preparation of layering liquid: A layering liquid is prepared by adding a hardly water-soluble drug, the micronized microcrystalline cellulose, an emulsifier, and necessary pharmaceutical additives to water and stirring the mixture sufficiently until dissolved or suspended. During stirring, a rotary disperser is preferably used to fully minimize the micronized microcrystalline cellulose and mix it with the other components. Examples of the disperser include "T.K. Homomixer", product of Tokushu Kika Kogyo Co., Ltd. and "ULTRA TURRAX", product of IKA Company. A stirrer having a weak stirring power such as propeller stirrer is not so preferred. In order to confirm dissolution or dispersion, components may be dispersed sequentially.

(c) Heating of spherical core particles and fluidized-bed coating apparatus: After spherical core particles are charged in a fluidized-bed coating apparatus, the core particles are fluidized (when the fluidized-bed coating apparatus is a tumbling fluidized-bed type is employed, the rotation portion of it is turned simultaneously) by supplying hot air from the bottom portion of the apparatus until an outlet-air temperature reaches a predetermined temperature.

(d) Coating with drug layer: The layering liquid is sprayed at a predetermined spray rate continuously or intermittently or at a rate raised in a stepwise fashion. The supply of the layering liquid is terminated when the coating amount reaches a predetermined amount.

(e) Drying of spherical base granules: The spherical base granules are dried while adjusting the amount of hot air and temperature (rotation speed of the rotating portion when a tumbling fluidized-bed type is employed) if necessary.

(f) Taking-out of spherical base granules: In the end, the resulting spherical base granules are taken out from the apparatus.

The spherical base granules obtained by the present invention can be used as granules, capsules, tablets or the like after subjected to particle size regulation and sustained release film coating, enteric film coating, or bitter-taste masking film coating if necessary.

Example 1

The present invention will next be described based on some examples. First, measuring methods of physical properties are described collectively.

<Sphericity [-] of Spherical Core Particles>

The shape of a sample is photographed using a digital microscope ("VH-7000", product of KEYENCE CORPORATION) (with a 50× or 100× lens) and a short diameter (D) and a long diameter (L) of 50 particles are measured using an image analyzer ("Image Hyper", product of Inter Quest). The terms "short diameter" and "long diameter" as used herein mean the length of a short side and the length of a long side of the smallest (in area) rectangle that circumscribes a boundary pixels of a particle, respectively. The sphericity is an average of a short diameter/long diameter (D/L) ratio <Average Short Diameter [μm] of Spherical Core Particles>

The average short diameter is a value at which the cumulative distribution of short diameter (D), which is determined in the same manner as the measuring method of sphericity, reaches 50%.

<Tapped Bulk Density [g/cm³] of Spherical Core Particles>

A 100-cm³ graduated cylinder is filled with 30 g of a sample and a tapped volume [cm³] after tapping about 30 times is measured. The bulk density is calculated in accordance with the following equation. This operation is performed three times and an average is adopted as a tapped bulk density.

Apparent tapped density [g/cm³]=30 [g]/tapped volume [cm³].

<Separation Condition [-] of Layering Liquid>

The layering liquid (30 cm³) is charged in a sample bottle having a diameter of 40 mm and a height of 50 mm and the state after five minutes is observed.

<Maximum Long Diameter and Short Diameter [μm] of Drug Particles>

A sample is prepared by dropping the layering liquid onto a slide glass and then, placing a cover glass thereon. The sample is photographed using an optical microscope (use of a 40× lens). Long diameter and short diameter of each of 50 drug particles on the photograph are measured and the maximum long diameter [μm] and maximum short diameter [μm] are determined.

<Particle Size [μm] of Micronized Microcrystalline Cellulose>

In the same manner as that employed for the preparation of the layering liquid, micronized microcrystalline cellulose is dispersed in purified water and a median diameter [μm] of the resulting dispersion is determined using a laser diffraction/scattering particle-size distribution analyzer ("LA-910", product of Horiba, Ltd.) while setting a specific refractive index at 1.20. The above operation is performed twice and an average is used.

<Recovery Ratio [% by Mass] of Spherical Base Granules>

The recovery ratio is determined in accordance with the following equation based on the recovery amount [g] of spherical base granules after layering and the total amount [g] of raw materials employed.

Recovery ratio [% by mass]={recovery amount [g]/total amount [g] of raw materials}×100

<Agglomeration Ratio [%] of Spherical Base Granules>

After dispersion of spherical base granules on paper, the number [a] of particles constituting agglomerated granules and the number [b] of single isolated particles are counted visually. The agglomeration ratio is calculated in accordance with the following equation. The number of particles observed is 1000 (=a+b).

Agglomeration ratio [%]={a/(a+b)}×100

Example 1

Preparation of Layering Liquid

While stirring 74.4 g of water in a rotary disperser ("T. K. Homomixer Mark II f model", product of Tokushu Kika Kogyo Co., Ltd.) at 5000 rpm, 15 g of povidone ("K-30", product of ISP Tec. Inc.) was added. The resulting mixture was stirred further until completely dissolved. Then, 0.1 g of a polyoxyethylene hydrogenated castor oil ("HCO-60", product of Nikko Chemicals Co., Ltd.) as an emulsifier was dispersed in the resulting solution until dissolved. 10 g of Ethenzamide ("Type A", product of API Corporation) was added in the resulting solution as a hardly water-soluble drug and then, 0.5 g of microcrystalline cellulose-carmellose sodium ("CEOLUS" RC-A591 NF, product of Asahi Kasei Chemicals Corporation) was added as a micronized microcrystalline cellulose, followed by dispersion for 30 minutes to prepare a layering liquid.

The resulting layering liquid was free from separation of the drug and foaming after completion of the dispersion and had considerably high suspension stability compared with that obtained in Comparative Example 1, which will be described later.

(Layering)

In a Wurster coating apparatus ("Multiplex" MP-01, equipped with a Wurster column, product of Powrex Corporation) was charged 0.3 kg of spherical core particles composed of 100% of microcrystalline cellulose ("Celphere" CP-203, product of Asahi Kasei Chemicals Corporation, sphericity: 0.9, tapped bulk density: 0.98 g/cm³, average short diameter: 165 µm) and the spherical core particles were layered until the layering amount reached 12.8% by mass (5.0% by mass in terms of the drug) under the conditions of a spray air pressure of 0.16 MPa, a spray air flow rate of 40 L/min, an inlet-air temperature of from 65 to 70° C., an outlet-air temperature of 40° C., an air flow rate of 40 m³/h, and a layering liquid spray rate of 3 g/min. The layering liquid was stirred with propeller constantly at 150 rpm. After the spraying of the layering liquid was terminated, drying was performed without changing the conditions until the outlet-air temperature increased to 42° C. A heater for inlet-air was then turned off and cooling was performed until the inlet-air temperature became 40° C.

Few powdered drug that did not attach to the spherical core particles were observed and almost all the amount of the granules was recovered. In addition, the granules thus obtained were almost free from agglomeration. The results are shown in Table 1.

Example 2

Layering

In a tumbling fluidized-bed coating apparatus ("Multiplex MP-01", product of Powrex Corporation) was charged 0.6 kg of spherical core particles which was the same as that used in Example 1 and they were layered with the layering liquid prepared in Example 1 until the layering amount became 12.8% by mass (5.0% by mass in terms of the drug) of the spherical core particles by using a tangential bottom spray under the conditions of a spray air pressure of 0.16 MPa, a spray air flow rate of 40 L/min, an inlet-air temperature of from 75° C., an outlet-air temperature of 41° C., an air flow rate of 35 m³/h, a rotation speed of a rotor of 400 rpm, and a layering liquid spray rate of 5.0 g/min. The layering liquid was stirred with propeller constantly at 150 rpm. After spraying of the layering liquid was terminated, the rotation speed of a rotor was decreased to 200 rpm and drying was performed until the outlet-air temperature reached 42° C. A heater for inlet-air was then turned off and cooling was performed until the inlet-air temperature became 40° C.

Few powdered drug that did not attached to the spherical core particles were observed. The resulting spherical base granules showed good results with a recovery ratio of 94.6% and an agglomeration ratio of 1.2%. The results are shown in Table 1.

Comparative Example 1

Preparation of Layering Liquid

While stirring 75.0 g of water in a rotary disperser ("T. K. Homomixer Mark II f model", product of Tokushu Kika Kogyo Co., Ltd.) at 5000 rpm, 15 g of povidone was added. The resulting mixture was stirred further until completely dissolved. Then, 10 g of ethenzamide was added and the resulting mixture was dispersed for 30 minutes to prepare a layering liquid.

The resulting layering liquid foamed severely and foams did not disappear even after the passage of time. Five minutes after completion of the preparation, precipitation of the drug occurred and the layering liquid had only poor suspension stability.

(Layering)

In the same manner as Example 1 except that the inlet-air temperature was raised to from 70 to 78° C. and layering liquid was stirred with propeller at 300 rpm, layering was performed.

A recovery ratio of the spherical base granules decreased because the drug did not attach to the spherical core particles and the powdered drug attached to a bug filter at the upper portion of the apparatus. Moreover, the spherical base granules thus obtained contained many agglomerated particles. The results are shown in Table 1.

TABLE 1

| | Formulation of layering liquid [% by mass] | | | | Ratio of drug particle size to average short diameter of core particles [%] (drug particle size [µm]) | | Results of layering | |
|---|---|---|---|---|---|---|---|---|
| | Hardly water-soluble drug [1] | Povidone | Micronaized microcrystalline cellulose [2] | Emulsifier [3] | Maximum long diameter | Maximum short diameter | Collection ratio [%] | Agglomeration ratio [%] |
| Ex. 1 | 10 | 15 | 0.5 | 0.1 | 17 (28) | 3 (5) | 95.3 | 3.8 |
| Ex. 2 | 10 | 15 | 0.5 | 0.1 | 17 (28) | 3 (5) | 94.6 | 1.2 |
| Comp. Ex. 1 | 10 | 15 | 0 | 0 | 16 (27) | 4 (6) | 89.5 | 7.7 |

[1] Hardly water-soluble drug: ethenzamide
[2] Micronized microcrystalline cellulose: microcrystalline cellulose-carmellose sodium
[3] Emulsifier: polyoxyethylene hydrogenated castor oil The spherical base granules obtained in Examples 1 and 2 by using the layering liquid comprising both a micronized microcrystalline cellulose and an emulsifier did not contain many agglomerated granules and showed a high recovery ratio.

In contrast, the spherical base granules obtained in Comparative Example 1 by using the layering liquid comprising neither a micronized microcrystalline cellulose nor an emulsifier, agglomerated due to foaming of the layering liquid and showed a low recovery ratio.

Referential Example

While stirring 89.4 g of water in a rotary disperser at 5000 rpm, 0.1 g of polyoxyethylene hydrogenated castor oil was added. The resulting mixture was stirred until completely dissolved. To the resulting solution were added successively 10 g of ethenzamide and 0.5 g of microcrystalline cellulose carmellose sodium which is the same as that employed in Example 1. The resulting mixture was dispersed for 30 minutes to prepare a layering liquid.

The layering liquid thus obtained was a uniform and highly clouded suspension free from foaming and precipitation of drug particles. The appearance of it is shown in FIG. 1. The observation results of the appearance are shown in Table 2.

Referential Comparative Example 1

While stirring 88.0 g of water in a rotary disperser at 5000 rpm, 2 g of povidone was added. The resulting mixture was stirred further until completely dissolved. In the resulting solution was added 10 g of ethenzamide, followed by dispersing for 30 minutes to prepare a layering liquid. The resulting layering liquid showed an uneven state with a foamy drug separated in the upper 53% portion of the liquid.

The appearance of the layering liquid is shown in FIG. 2. The observation results of the appearance are shown in Table 2.

Referential Comparative Example 2

In the same manner as Referential Comparative Example 1 except that the amount of povidone was 15 g, a layering liquid was prepared. The separation state of the liquid was observed. Although the drug amount present in the lower layer increased compared with that in Referential Comparative Example 1, the foamy drug layer in the upper portion was still present without decreasing.

The appearance of the layering liquid is shown in FIG. 3. The observation results of the appearance are shown in Table 2.

Referential Comparative Example 3

While stirring 89.5 g of water in a rotary disperser at 5000 rpm, 0.1 g of polyoxyethylene hydrogenated castor oil was added. The resulting mixture was stirred further until completely dissolved. In the resulting solution was added 10 g of ethenzamide, followed by dispersion for 30 minutes to obtain a layering liquid.

The resulting layering liquid was separated into three layers. The upper 23% layer contained foams, while the lower 23% layer contained a drug precipitation layer. The appearance of the liquid is shown in FIG. 4. The observation results of the appearance are shown in Table 2.

Referential Comparative Example 4

In the same manner as Referential Comparative Example 3 except that 0.3 g of polyoxyethylene hydrogenated castor oil was added to 89.7 g of water, a layering liquid was prepared.

The lower 11% layer was a drug precipitation layer, showing a little improvement compared with Referential Comparative Example 3 but a problem of three-layer separation does not resolved. The observation results of the appearance are shown in Table 2.

Referential Comparative Example 5

While stirring 89.4 g of water in a rotary disperser at 5000 rpm, 0.5 g of microcrystalline cellulose-carmellose sodium was added. The resulting mixture was dispersed for 30 minutes. In the resulting dispersion was added 10 g of ethenzamide, followed by dispersion for 30 minutes to prepare a layering liquid.

The layering liquid thus obtained showed an uneven state with a foamy drug layer in the upper 52% portion of the liquid as in Referential Comparative Example 1. The observation results of the appearance are shown in Table 2.

Referential Comparative Example 6

In the same manner as Referential Comparative Example 5 except that 2.2 g of microcrystalline cellulose-carmellose sodium which is the same as that used in Example 1 was added to 87.8 g of water, a layering liquid was prepared.

The layering liquid thus obtained showed a uniform state without separation, but it became a gel due to the addition of a large amount of microcrystalline cellulose carmellose sodium. The resulting gel was so tacky and it was difficult to transfer the layering liquid via a tube pump. The appearance is shown in FIG. 5. The observation results of the appearance are shown in Table 2.

TABLE 2

| | Formulation of layering liquid [% by mass] | | | | Observation results of appearance of layering liquid | |
|---|---|---|---|---|---|---|
| | Hardly water-soluble drug [1] | Povidone | Micronized microcrystalline cellulose [2] | Emulsifier [3] | Separation state | Observation results (vol. %) |
| Ref. Ex. | 10 | 0 | 0.5 | 0.1 | No separation | Uniform and highly clouded suspension |
| Ref. Comp. Ex. 1 | 10 | 2 | 0 | 0 | Two-layer separation | Upper layer (53%) Foamy drug<br>Lower layer (47%) Clear liquid |
| Ref. Comp. Ex. 2 | 10 | 15 | 0 | 0 | Two-layer separation | Upper layer (53%) Foamy drug<br>Lower layer (47%) Lightly clouded liquid |
| Ref. Comp. Ex. 3 | 10 | 0 | 0 | 0.1 | Three-layer separation | Upper layer (23%) Foam<br>Intermediate layer (54%) Lightly clouded liquid<br>Lower layer (23%) Precipitated drug |
| Ref. Comp. Ex. 4 | 10 | 0 | 0 | 0.3 | Three-layer separation | Upper layer (19%) Foam<br>Intermediate layer (70%) Highly clouded liquid<br>Lower layer (11%) Precipitated drug |
| Ref. Comp. Ex. 5 | 10 | 0 | 0.5 | 0 | Two-layer separation | Upper layer (52%) Foamy drug<br>Lower layer (48%) Lightly clouded liquid |
| Ref. Comp. Ex. 6 | 10 | 0 | 2.2 | 0 | No separation | Uniform and highly clouded gel |

[1] Hardly water-soluble drug: ethenzamide
[2] Micronized microcrystalline cellulose: microcrystalline cellulose-carmellose sodium
[3] Emulsifier: polyoxyethylene hydrogenated castor oil The layering liquid obtained in Referential Example by using micronized microcrystalline cellulose and an emulsifier in combination was a uniform suspension.

In contrast, the layering liquids comprising neither micronized microcrystalline cellulose nor emulsifier separated into two layers (Referential Comparative Examples 1 and 2). The layering liquids comprising the emulsifier but not comprising the micronized microcrystalline cellulose foamed severely and separated into three layers (Referential Comparative Examples 3 and 4). The layering liquid comprising the micronized microcrystalline cellulose but not comprising the emulsifier did not foam and the layer separation was partially resolved (Referential Comparative Example 5). In order to completely resolve the problem of separation, however, it was necessary to increase the amount of micronized microcrystalline cellulose to the extent that it made the layering liquid into gel and thus made it unsatisfactory as a layering liquid (Referential Comparative Example 6).

From the above results, it has been confirmed that the layering liquid comprising a hardly water-soluble drug has improved suspension stability when both micronized microcrystalline cellulose and an emulsifier are added in combination to the liquid.

INDUSTRIAL APPLICABILITY

The production method of the present invention is suited in the field of the production of film-coated pharmaceutical granules.

Figure 1:
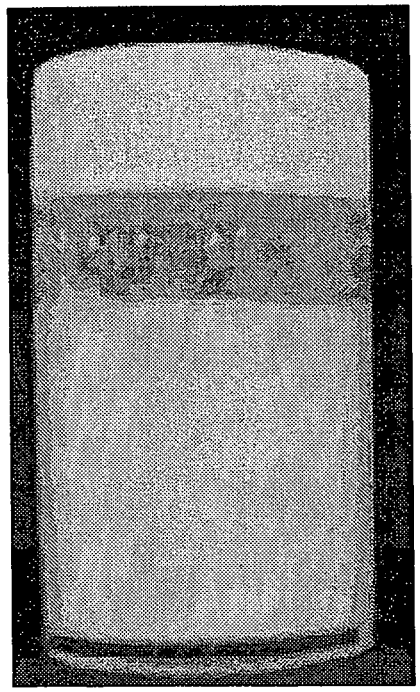
FIG. 1 The appearance of the layering liquid prepared in Referential Example.
Figure 2:
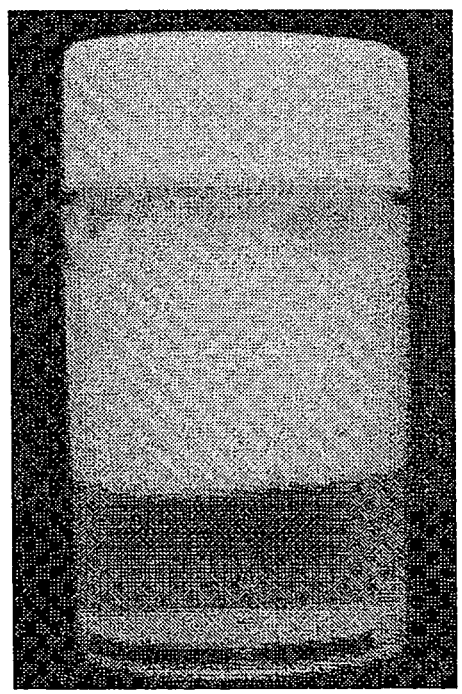
FIG. 2 The appearance of the layering liquid prepared in Referential Comparative Example 1.
Figure 3:
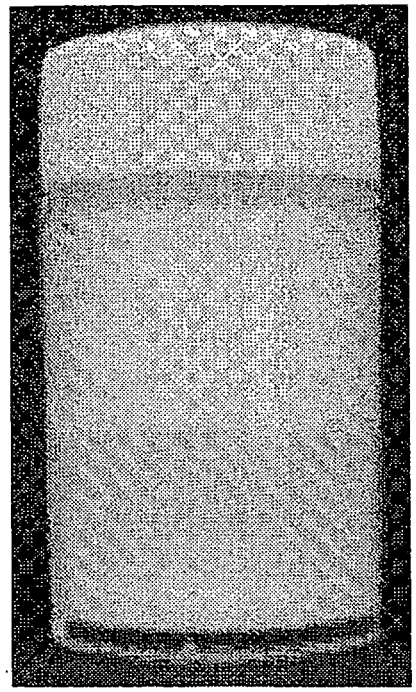
FIG. 3 The appearance of the layering liquid prepared in Referential Comparative Example 2.
Figure 4:
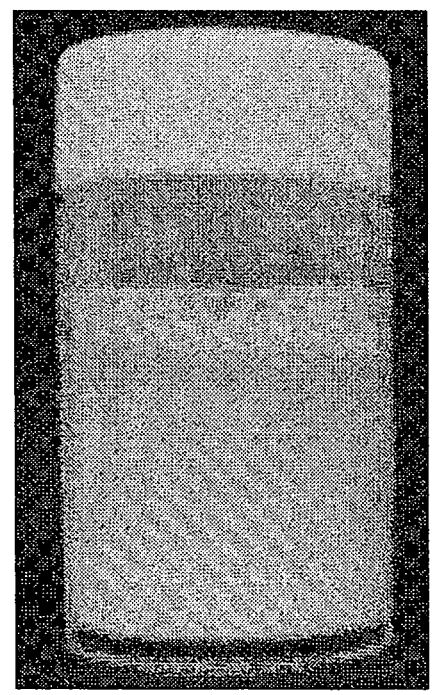
FIG. 4 The appearance of the layering liquid prepared in Referential Comparative Example 3.
Figure 5:
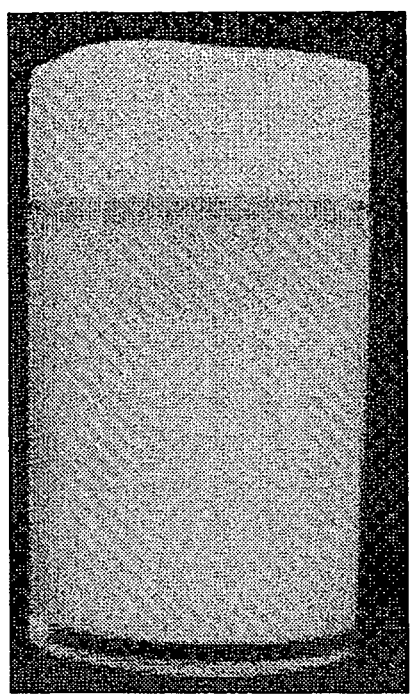
FIG. 5 The appearance of the layering liquid prepared in Referential Comparative Example 6.

The invention claimed is:

1. A production method of a pharmaceutical product, comprising:
    providing pharmaceutically inert elliptical core particles having a minor axis/major axis ratio of 0.7 or greater; and
    spraying a layering liquid on the core particles, thereby coating the core particles with a drug-containing layer, wherein the layering liquid comprises:
        (1) from 0.01 to 50% by mass of hardly water-soluble drug particles having a maximum major axis of not greater than 30% of an average minor axis of the core particles and a maximum minor axis of not greater than 12% of the average minor axis of the core particles;
        (2) from 0.1 to 2% by mass of a micronized microcrystalline cellulose; and
        (3) from 0.01 to 1% by mass of an emulsifier,
    wherein the hardly water-soluble drug is any one selected from the group consisting of amcinonide, ibuprofen, indomethacin, ethenzamide, cefotiam hexetil hydrochloride, nicardipine hydrochloride, omeprazole, prednisolone valerate acetate, diflucortolone valerate, dexamethasone valerate, betamethasone valerate, clarithromycin, griseofulvin, clonazepam, chloramphenicol, synthetic peptide compounds, cortisone acetate, diflorasone diacetate, dexamethasone acetate, triamcinolone acetate, paramethasone acetate, hydrocortisone acetate, fludrocortisone acetate, methylprednisolone acetate, diazepam, digitoxin, digoxin, difluprednate, beclometasone dipropionate, betamethasone dipropionate, sulpiride, sulfathiazole, cefuroxime axetil, dexamethasone, triamcinolone, triamcinolone acetonide, nicardipine, nifedipine, nilvadipine, noscapine, halcinonide, hydrocortisone, flumetasone pivalate, phenacetin, phenitoin, budesonide, prazepam, fluocinonide, fluocinolone acetonide, fluorometholone, fludroxycortide, prednisolone, alclometasone dipropionate, clobetasol propionate, dexamethasone propionate, deprodone propionate, betamethasone, migrenin, methylprednisolone, ubidecarenone, clobetasone butyrate, hydrocortisone butyrate, hydrocortisone butyrate propionate, riboflavin butyrate, lansoprazole, and riboflavin.

2. The production method according to claim 1, wherein the maximum major axis of the hardly water-soluble drug particles are not greater than 20% of the average minor axis of the core particles and the maximum minor axis of the hardly water-soluble drug particles are not greater than 10% of the average minor axis of the core particles.

3. The production method according to claim 1 or 2, wherein the layering liquid comprises from 1 to 30 mass % of the hardly water-soluble drug particles.

4. The production method according to claim 1 or 2, wherein the layering liquid comprises from 5 to 20 mass % of the hardly water-soluble drug particles.

5. The production method according to claim 1 or 2, wherein the layering liquid comprises from 0.2 to 1 mass % of the micronized microcrystalline cellulose.

6. The production method according to claim 1 or 2, wherein the layering liquid comprises from 0.3 to 0.8 mass % of the micronized microcrystalline cellulose.

7. The production method according to claim 1 or 2, wherein the layering liquid comprises from 0.05 to 0.8 mass % of the emulsifier.

8. The production method according to claim 1 or 2, wherein the emulsifier is polyoxyethylene hydrogenated castor oil 60.

9. The production method according to claim 1 or 2, wherein the micronized microcrystalline cellulose has an average particle size of 9 μm or less.

10. The production method according to claim 1 or 2, wherein the core particles have a microcrystalline cellulose content of 70 mass % or greater.

11. The production method according to claim 1 or 2, wherein the core particles have a bulk density of from 0.5 to 1.0 g/cm$^3$.

12. The production method according to claim 1, wherein:
    coating the core particles with the drug-containing layer produces base granules, and
    the method further comprises forming a film on the base granules, the film being selected from the group consisting of a sustained release film, an enteric film, and a bitterness-masking film.

13. The production method according to claim 1, wherein the the hardly water-soluble drug is any one selected from the group consisting of amcinonide, ethenzamide, cefotiam hexetil hydrochloride, nicardipine hydrochloride, omeprazole, griseofulvin, clonazepam, chloramphenicol, synthetic peptide compounds, diazepam, digitoxin, digoxin, sulpiride, sulfathiazole, cefuroxime axetil, nicardipine, nifedipine, nilvadipine, noscapine, halcinonide, phenacetin, phenitoin, prazepam, deprodone propionate, migrenin, ubidecarenone, riboflavin butyrate, lansoprazole, and riboflavin.

14. The production method according to claim 1 or 2, wherein the micronized microcrystalline cellulose comprises microcrystalline cellulose-carmellose sodium.

* * * * *

UNITED STATES PATENT AND TRADEMARK OFFICE
CERTIFICATE OF CORRECTION

| | | |
|---|---|---|
| PATENT NO. | : 9,095,512 B2 | Page 1 of 1 |
| APPLICATION NO. | : 12/310067 | |
| DATED | : August 4, 2015 | |
| INVENTOR(S) | : Yoshihito Yaginuma et al. | |

It is certified that error appears in the above-identified patent and that said Letters Patent is hereby corrected as shown below:

Title Page, Item (56) OTHER PUBLICATIONS, Line 1

Delete "Olsalzaine" and insert --Olsalazine--, therefor.

Claims

Claim 13, Column 14, Line 61

Delete "the the" and insert --the--, therefor.

Signed and Sealed this
First Day of December, 2015

Michelle K. Lee
*Director of the United States Patent and Trademark Office*